United States Patent [19]

Bookwalter

[11] Patent Number: 4,926,877
[45] Date of Patent: May 22, 1990

[54] BIOPSY NEEDLE WITH COMPLETELY CLOSABLE CUTTING END BORE

[76] Inventor: John R. Bookwalter, 9 Belmont Ave., Brattleboro, Vt. 05301

[21] Appl. No.: 342,198

[22] Filed: Apr. 24, 1989

[51] Int. Cl.$^5$ .............................................. A61B 10/00
[52] U.S. Cl. .................................... 128/754; 606/184; 606/185
[58] Field of Search ............... 128/749, 751, 752, 753, 128/754, 305, 310; 606/167, 184, 185

[56] References Cited

U.S. PATENT DOCUMENTS

| | | | |
|---|---|---|---|
| 3,007,471 | 11/1961 | McClure, Jr. | 128/754 |
| 4,651,752 | 3/1987 | Fuerst | 128/754 |
| 4,785,826 | 11/1988 | Ward | 128/754 |

*Primary Examiner*—Max Hindenburg
*Assistant Examiner*—Randy Shay
*Attorney, Agent, or Firm*—Sughrue, Mion, Zinn, Macpeak & Seas

[57] ABSTRACT

A hollow tubular needle body open at a distal end, tapers inwardly to define a distal end opening of reduced cross-section relative to the balance of the biopsy needle hollow tubular body bore. The distal end of the hollow tubular needle body is provided with an axially oblique sharp cutting edge terminating in a pointed tip to facilitate skin penetration. A hollow tubular needle body is of racetrack cross-section, formed by opposed parallel straight walls joined at opposite ends to respective arcuate walls. Laterally projecting ribs provided within the hollow tubular needle body at the juncture between one arcuate wall and the opposed, parallel straight walls support a thin flexible strip formed guillotine cutting blade, having a lateral width less than the distance between the opposed parallel straight body walls facing the one arcuate wall for longitudinal sliding movement toward and away from the needle body distal end. The blade width is in excess of the width of the distal end opening, and the blade terminates in a transverse arcuate leading edge conforming to the arcuate shape of the hollow tubular needle body distal end arcuate wall with which it contacts, to insure sealing of the blade as it traverses across the distal end opening parallel to the oblique distal end cutting edge and to effect complete severance of tissue within the bore. The racetrack configuration of the needle body permits orientation of the needle while insuring severance of a full section of biopsy tissue at the very tip of the needle.

6 Claims, 2 Drawing Sheets

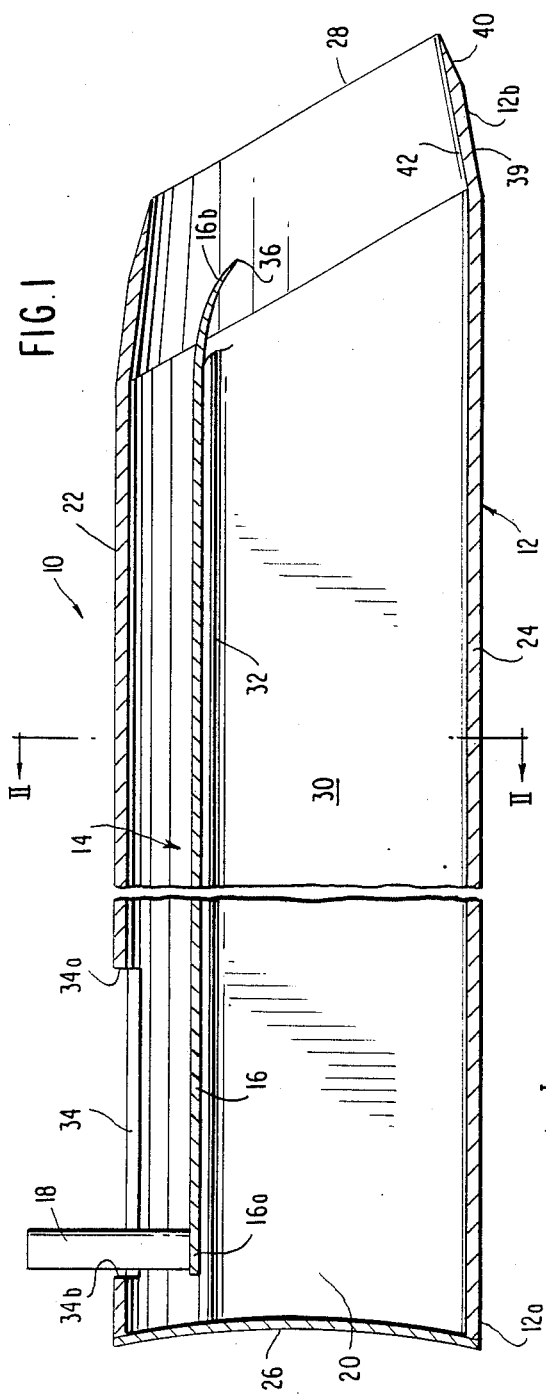
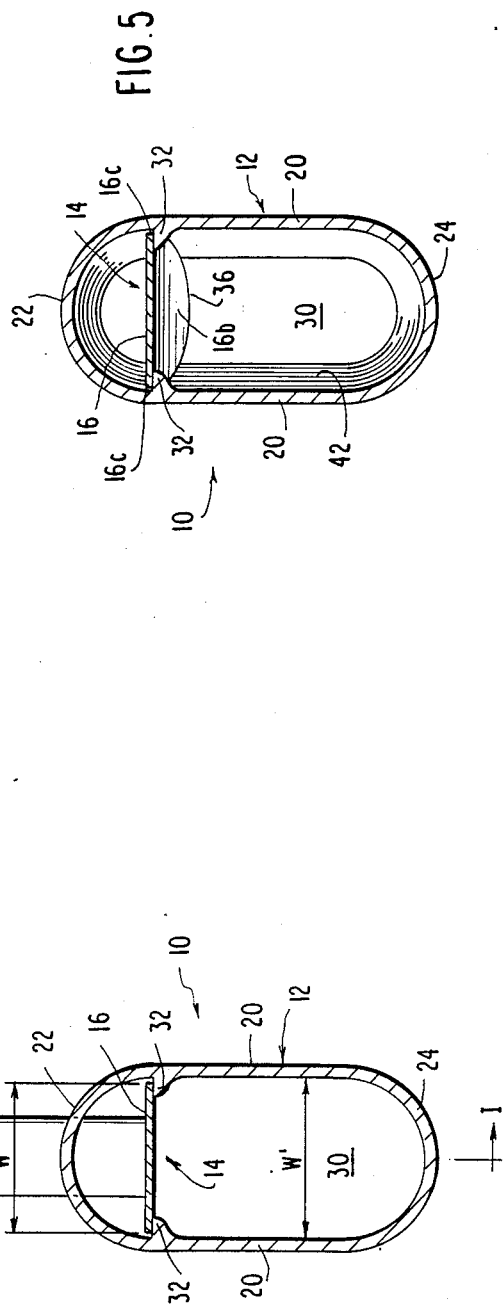

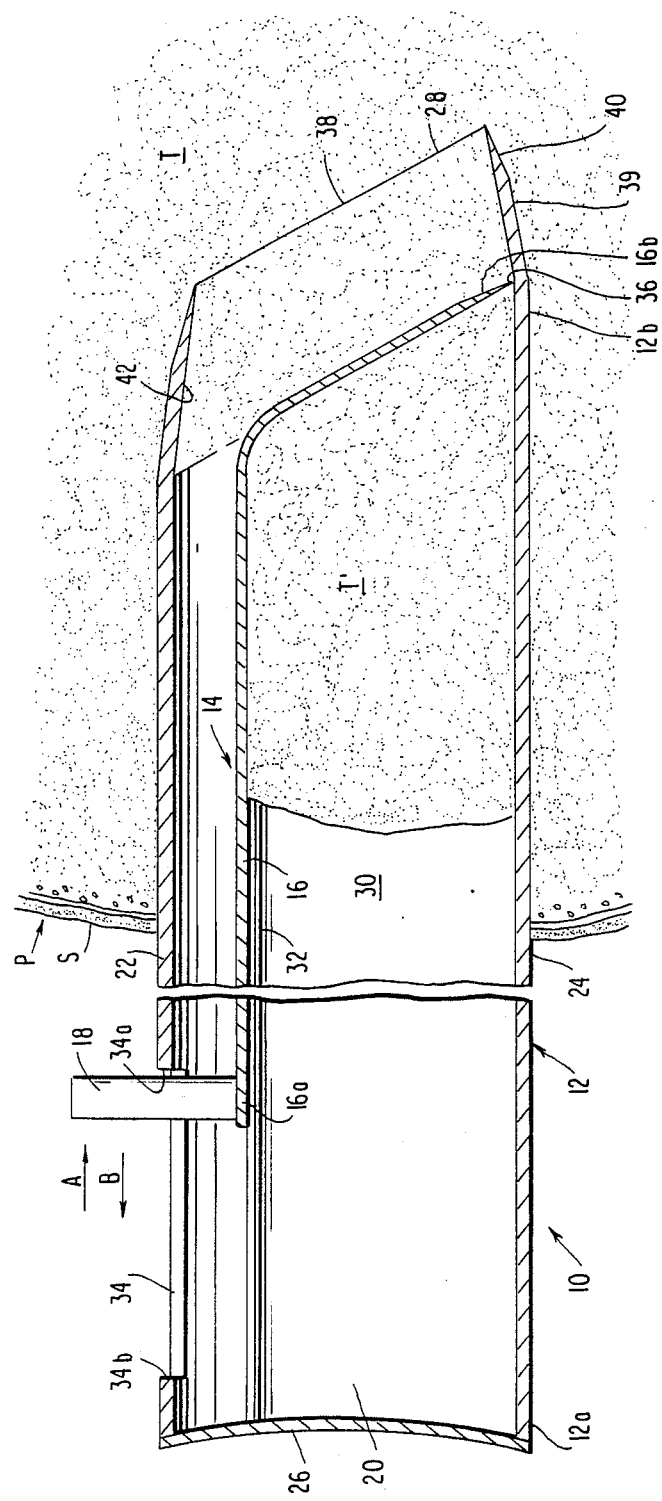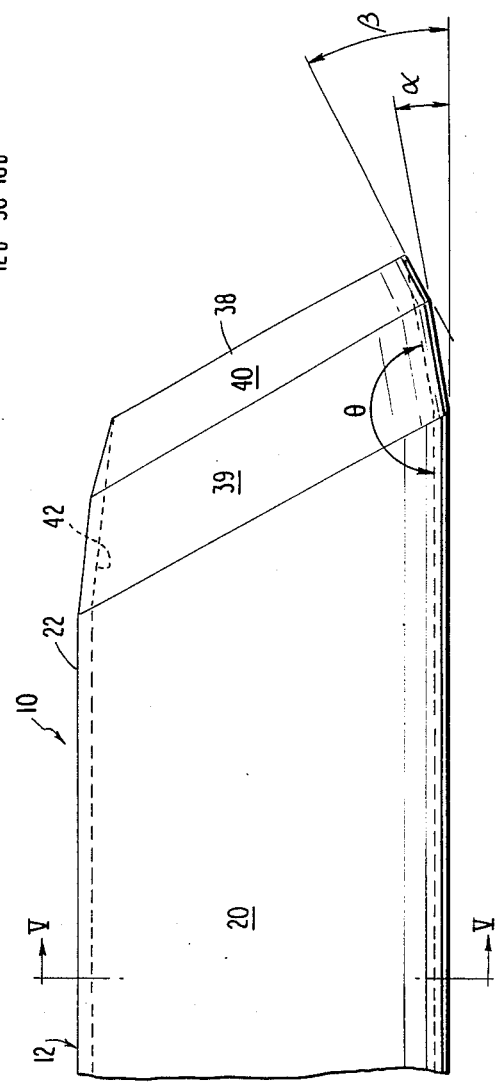

BIOPSY NEEDLE WITH COMPLETELY CLOSABLE CUTTING END BORE

FIELD OF THE INVENTION

This invention relates to biopsy needles taking the form of a small hollow tube sharpened at a distal end, carrying internally a guillotine-type sliding cutting blade, and more particularly to an improved biopsy needle in which the sharpened distal end has its bore completely closed off by the sliding cutter.

BACKGROUND OF THE INVENTION

A biopsy needle is employed by a physician to remove from a patient a small piece of tissue permitting the tissue to be subsequently examined pathologically in order to determine the condition of the tissue, particularly with respect to the existence of undesired cells.

The excision of tissue should be achieved with minimum injury to the balance of the tissue. Attempts have been made to employ a flexible, reciprocating blade within a support or housing which penetrates the portion of the body being examined with a portion of the tissue penetrating the interior of the body prior to advancing the blade or stylus whose cutting edge severs the tissue internally of the body and retains it during removal or retrieval of the needle. U.S. Patents representative of such procedure and instruments employed therein are U.S. Pat. Nos. 1,564,356: 2,131,780: 3,007,471: 3,407,815 and 4,651,752.

U.S. Pat. No. 4,651,752 to Fuerst, issuing Mar. 24, 1987 is directed to such a biopsy needle in an attempt to obtain a specimen which fills the entire volume of a recess within the needle sheath or hollow tubular body and which effectively cuts the tissue clearly and retains it securely for safe retrieval. In attempting to reach that end, the cutting action provided is essentially clean, occurring at the base of the incursion with little or no tearing of the tissue. While the biopsy needle of Fuerst is an advancement in the art, the cross-sectional configuration of the tubular needle body is circular, a wall of the circular cross-section tubular body is flattened to one side and a thin, rectangular flexible blade is slidably mounted on the body, to close off an opening within the body itself over the length of the body. Further the blade terminates in a triangular shape tip in an attempt to close off the oblique cutting edge at the distal end of the needle body, with edges of the tip received within opposed grooves within the body running the length of the body to the sides of opening toward the sharpened point of that body. The biopsy needle of Fuerst has several deficiencies. First of all, the needle body is open at its side opposite that of the distal end tip, and the sliding blade makes contact between the blade and the patient tissue over its complete length. Secondly, with the blade retracted, transfer of fluids may occur between the bore of the needle and the tissue. Additionally, the planar configuration of the needle body cutting edge at the distal end is curved or arcuate over the complete extent of the same, inherently preventing the cutting blade from closing off the biopsy needle body at its distal end and preventing the cutting blade from neatly and cleanly severing the tissue encased by the needle and completely closing off the bore of the biopsy needle during tissue severence.

It is therefore a primary object of the present invention to provide an improved biopsy needle which is relatively small in size, simple in construction, which employs a hollow tubular biopsy needle body whose transverse section inherently provides a greater cross-section of area for amassing severed tissue during operation of the reciprocal guillotine blade, wherein the sharp cutting edge of the needle body distal end is at the inside surface of the tubular body, wherein the reciprocating blade is effectively guided during its complete extent of movement from retracted to extended, cutting position and vice versa in lateral straight edge sealed contact with the interior of the hollow needle body, wherein the blade is always within the bore of the needle to maximize safety to the physician using the instrument, wherein there are no moving parts on the outer surface portion of the needle body in contact with the tissue beneath the patient's skin, and wherein the shape of the tubular needle body facilitates orientation of the needle in the tissue relative to the location of the blade internally and its reciprocation path, and which insures severence of a full section of biopsied tissue at the very tip of the needle.

SUMMARY OF THE INVENTION

The invention is directed to an improved biopsy needle having a hollow tubular body with a proximate or hub end, and an open distal end. The hollow tubular needle body is of racetrack cross section, defined by laterally opposed parallel straight walls integrally joined along opposite edges by respective opposed arcuate walls. The distal end of said hollow tubular needle body is provided with an axially oblique, sharp cutting edge terminating in a pointed tip. At least the straight walls of said hollow tubular needle body narrow toward each other at said body distal end to form a reduced lateral width bore at the open distal end of said hollow tubular needle body. Guide means are provided within the hollow tubular needle body at the juncture between one arcuate wall and the opposed, parallel straight walls. A flexible strip form guillotine cutting blade with a width less than the distance between the opposed parallel straight body walls is positioned between the guide means and said one arcuate wall for longitudinal sliding movement toward and away from the distal end. The flexible guillotine cutting blade has a width in excess of the width of the narrow, straight walls of said body at said distal end opening, and said blade terminates in a transverse arcuate leading edge conforming to the arcuate shape of the other arcuate wall of said hollow tubular needle body distal end.

Preferably both said arcuate walls of said hollow tubular needle body at said distal end also narrow toward each other to reduce the complete cross-sectional area of said bore at the distal end opening to insure the complete sealing off of said body distal end opening when said blade is at its full projected position. The narrowing of the distal end of the bore serves to automatically deflect the flexible cutting blade so that the end of the blade traverses across the bore parallel to the oblique distal end cutting edge to insure complete severance of the tissue within the bore with the leading edge of the blade of curved configuration conforming to that of the other of said arcuate walls.

A longitudinal slot may be provided within the hollow tubular needle body at said hub end thereof, and a thumb actuator fixed at one end to the blade remote from its cutting edge projects outwardly through the longitudinal slot for thumb actuation externally of the hollow tubular needle body. Preferably the slot is completely covered and sealed off by a collar which surrounds the needle body to permit suction to be applied to the hub of the needle, during the taking of the biopsy to facilitate entry of the tissue into the bore of the needle during needle body distal end penetration beneath the patient's skin. The racetrack configuration of the needle body permits orientation of the needle while insuring the severence of a full section of biopsied tissue at the very tip of the needle. The guide means may include integrally formed, oppositely directed projections on the inner surface of the straight, parallel sides of the needle body where the sides integrally join said one arcuate wall.

Other objects and features of the invention will be apparent in the following description and claims, in which the invention is described, together with details to enable one of ordinary skill in the art to practice the invention all in connection with the best mode presently contemplated for the invention.

BRIEF DESCRIPTION OF THE DRAWINGS

FIG. 1 is a longitudinal, vertical, sectional view of a biopsy needle forming a preferred embodiment of the invention, taken about lines I—I of FIG. 2, with the cutting blade in retracted position.

FIG. 2 is a sectional view of the biopsy needle of FIG. 1 taken about line II—II.

FIG. 3 is a vertical sectional view of the biopsy needle similar to that of FIG. 1, during use after penetration into the skin of the patient and with the flexible guillotine blade in projected position to effect severence of the tissue.

FIG. 4 is an enlarged view of the distal end of the biopsy needle body forming a principle element of the biopsy needle of FIG. 1.

FIG. 5 is an end view of the biopsy needle of FIG. 4, toward the distal cutting end, and illustrating the racetrack cross-sectional configuration thereof.

DETAILED DESCRIPTION OF THE PREFERRED EMBODIMENT

Referring to the drawings, there is shown a preferred embodiment of the invention in which the biopsy needle, indicated generally at 10, is depicted in a somewhat shortened and transversely enlarged form for a better understanding of the invention. However, in actual practice, such biopsy needles are of relatively small diameter and of extended length with respect to their transverse dimension. The biopsy needle 10 consists of two main parts, a hollow, tubular needle body indicated generally at 12 and a cutting blade assembly indicated generally at 14. The cutting blade assembly consists of a thin, flexible, strip form metal cutting blade 16 and a thumb actuator 18, fixedly mounted to or integrally formed with the cutting blade 16 at the end 16a of the cutting blade remote from its opposite, sharp cutting end 16b.

The cutting blade 16 has a width W which is slightly less than the lateral width W between the straight, vertical side walls 20 of the hollow tubular needle body 12, FIG. 2. In the preferred embodiment, the needle body which may be formed of stainless steel or the like, is characterized by having a cross-sectional configuration which is of racetrack form, including integrally the laterally opposed straight, parallel, vertical side walls 20 joined integrally by an arcuate top wall 22, and an arcuate bottom wall 24 of the same configuration and size, FIGS. 2, 5. The proximate hub end 12a of the needle body 12 is preferably open at 26 while the opposite, distal end 12b is provided with a reduced cross sectional area opening 28. Bore 30 extends the length of the body, and functions to receive tissue prior to blade cutting during operation of the biopsy needle by penetration into the flesh in a manner similar to that described in U.S. Pat. No. 4,651,752.

The racetrack cross-sectional configuration given to needle body 12 forms a principle aspect of the present invention. Not only is it of distinctive shape in cross-section, but it facilitates the complete closure of the distal end opening 28. Additionally, it avoids any sliding contact between the blade 16 and the patient tissue, except at the tissue severence area at opening 28 at the distal end 12b of the needle body 12. Utilizing the unique geometric shape as per FIGS. 2 and 5 which is partially rectangular, but with arched, curved or arcuate top and bottom walls 22, 24 assures that the cutting blade 16 will neatly and cleanly sever the tissue encased by the needle body 12.

To facilitate that action, in the preferred embodiment of the invention as seen in FIG. 2, the metal tubular needle body is provided with molded machined or extruded form guide tracks 32 which laterally oppose each other and project inwardly into bore 30 from opposite sides and at the juncture between the upper edges of the laterally opposed side walls 20 of the hollow tubular needle body 12, and the arcuate top wall 22. The distance between the ends of the opposed guide tracks 32 which take the form of internal, integral ribs, is less than the lateral width W of the flexible guillotine cutting blade 16. Additionally, the top wall 22 of the needle body is provided with a longitudinal slot 34 which extends from near the proximate end 12a towards the distal end of the body over a length necessary to permit the cutting blade 16 to be shifted from its full retracted position shown in FIG. 1 to its full extended, tissue severence position shown in FIG. 3 where the sharp leading edge 36 of the blade 16 strikes the bottom Wall 24 of the needle body 12, thereby closing off the distal end opening 28 of the needle body, FIG. 3. The length of the blade 16 is such that the thumb actuator 18 approaches but does not come into full contact with the end 34a of the slot 34 and with blade movement terminated by contact between the leading edge 36 of the cutting blade and the bottom wall 24 of the tubular needle body 12.

Reference to FIG. 5 shows the curved leading edge 36 of the thin flexible blade 16, the leading edge 36 preferably having an arcuate configuration matching that of the interior surface of the needle body bottom wall 24 with which it comes into contact when in the cutting blade full extended position, FIG. 3. As may be appreciated, where the upper and lower walls 22, 24 of tubular needle body 12 are circular, the radius of curvature of the bottom wall 24, on its inner surface, matches that of the leading edge 36 of blade 16.

It should be appreciated that the distal end 16b of blade 16 functions not only as a cutting blade, but also as a closure for the distal end opening 28 of the tubular needle body 12. In order to facilitate the sealed closure of the distal end 16b of the cutting blade during the tissue cutting action of the instrument, bore 30 is of reduced size at the distal end 12b of the tubular needle body 12, as shown best in FIGS. 4 and 5. Preferably, there is provided a double external taper of the outside surface of distal end 12b. The needle body bore 30 tapers at portion 42 uniformly at the same obtuse angle $\theta$ from some point just rearwardly of the oblique cutting edge 38, while a double taper is provided to the exterior surface of the needle body distal end 12a. The first tapered external surface 39 at an angle α such that the surface on the exterior of the first tapered outer wall portion 38a of the tubular needle body 12 extends parallel to the slope of the tapered narrowing internal bore wall 42. The second tapered external surface portion 40 of the tubular needle body is at an increased angle β and defines a sharp cutting edge 36 with the tapered portion of the bore 30. It should be noted that the double taper of the preferred embodiment extends over both lateral side walls, top wall 22 and bottom wall 24 of the tubular needle body 12 thus uniformly providing a narrowing of the biopsy needle body 12 both top to bottom and laterally from side to side, as per FIG. 5. The narrowed distal end 12b of the needle body 12 functions to confine the distal end 16b of blade 16 within the needle body as it moves forwardly toward the distal end opening 28 of the instrument. Since the blade 16 is rectangular over much of its length, and only the leading edge 36 is curved, the distal end 16b is prevented from moving outwardly of opening 28 at the top, and opposed side edges 16c of the blade 16 contact the inside wall surfaces of the double tapered portion of the tubular needle body 12 at its distal end 12b, forcing the distal end 16b of the blade to move downwardly at an angle parallel to that of the oblique cutting edge 38 of the biopsy needle body 12. FIG. 3 until the arcuate leading edge 36 of the blade abuts the inner surface 42 of the double tapered distal end bottom wall 24 of the tubular needle body 12.

Reference to FIG. 3 shows the operation of the needle or instrument 10 during its use. In an exemplary mode of operation, the flexible guillotine assembly is placed in the position shown in FIG. 3, that is, with the arcuate cutting edge 36 of the blade in its fully projected position in contact with the bottom wall 24 of the tubular needle body 12 as per arrow A, FIG. 3. The needle body 12 is then projected into the flesh of the patient P, with oblique cutting edge 38 through penetrating surface (skin) S. When the perimeter of the tissue T to be diagnosed is reached, the bore 30 at the distal end of the needle body is opened by sliding the cutting blade 16 rearwardly, as per arrow B, from the closed position, at which point until the thumb actuator 18 contacts the end 34b of slot 34, FIG. 3, at which point the blade 16 occupies the position shown in FIG. 1. At this point, further insertion or distal end 16 at 12b of the needle body 12 causes cutting edge 38 to advance into the tissue T to a desired depth and the tubular needle body isolates (sets up) the tissue T' to be severed. By thumb actuation, the thumb actuator 18 is advanced to the position shown in FIG. 3, again in the direction of arrow A and the leading edge 36 of the cutting blade severs the tissue T' from the mass T of surrounding tissue. Blade 16 sealably closes off opening 28 at the distal end of body 12 with the distal end 16b of the blade curving obliquely downwardly during forward movement of thumb actuator 18 due to the side edges 16c of the blade contacting the vertical narrowed bore surfaces 42 at the distal end of the body 12 and or the curved leading edge 36 of blade 16 contacting the inside surfaces of top wall 22 where it bends inwardly at the distal end 12a of the needle body 12. The tissue specimen is thus cleanly separated from the host tissue, trapped within the bore 30 of the instrument body 12, and the needle 10 may be withdrawn without tearing of any of the surrounding tissue T.

What is claimed is:
1. A biopsy needle for penetrating, severing and removing tissue specimens comprising:
   a hollow tubular needle body of racetrack cross-section, having a proximate hub end, and an open, distal end, said hollow tubular needle body being defined by laterally opposed, parallel straight walls integrally joined along opposite edges by respective, opposed arcuate walls, said distal end of said hollow tubular needle body terminating in an axially oblique, sharp cutting edge forming a pointed tip, at least the straight walls of said hollow tubular needle body narrowing toward each other at said body distal end to form a reduced lateral width bore, guide means provided within the hollow tubular needle body at the juncture between one arcuate wall and the opposed parallel straight walls, a thin flexible strip form metal, guillotine cutting blade of a width less than the distance between the opposed parallel straight body walls positioned between said guide means and said one arcuate wall for longitudinal sliding movement toward and away from said distal end, said flexible guillotine cutting blade having a width in excess of the distal end opening within said hollow tubular needle body such that said flexible guillotine cutting blade is prevented from projecting through said distal end opening, and is deflected toward said tip during sliding movement in a direction tending to close off said opening, said guillotine cutting blade terminating in a transverse curved leading edge conforming to the curvature of the hollow tubular needle body distal end other arcuate wall, and
   means carried by said blade to shift said blade between an axially projected position wherein said flexible guillotine cutting blade closes off said distal end opening and a retracted position where tubular needle body distal end is open to receive tissue to be severed.
2. The biopsy needle as claimed in claim 1, wherein said arcuate walls narrow toward each other at said open distal end of said hollow tubular needle body to form a continuous reduced cross-sectional area portion at said open distal end of said hollow tubular needle body.
3. The biopsy needle as claimed in claim 2, wherein the hollow tubular needle body tapers uniformly inwardly at said distal end just rearwardly of the oblique cutting edge to capture said axially slidable cutting blade and to effect sealed engagement of the edges of said blade with the needle body bore at said distal end opening to facilitate complete severence of tissue within the bore.
4. The biopsy needle as claimed in claim 3, wherein the hollow tubular needle body at said distal end, is provided with an external double tapered surface toward the axis of the hollow tubular needle body to form said cutting edge at the inside surface of the hollow tubular needle body, defining the distal end opening thereof.
5. The biopsy needle as claimed in claim 1, further including a longitudinal slot within said hollow tubular needle body, adjacent the hub end thereof, and wherein said means for shifting said blade between projected and retracted positions comprises a thumb actuator fixed at one end to the thin flexible cutting blade proximate to said needle body hub, and projecting radially outwardly through said longitudinal slot for thumb actuation externally of the hollow tubular needle body.

6. The biopsy needle as claimed in claim 1, wherein said guide means comprises integrally formed, oppositely directed projections on the inner surface of the straight parallel sides of said needle body, where said sides are integrally joined to said one arcuate wall.

* * * * *